US 9,165,385 B2

(12) United States Patent
Erhard et al.

(10) Patent No.: US 9,165,385 B2
(45) Date of Patent: Oct. 20, 2015

(54) IMAGING PROCEDURE PLANNING

(75) Inventors: Klaus Erhard, Hamburg (DE); Michael Grass, Hamburg (DE); Dirk Schaefer, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 243 days.

(21) Appl. No.: 13/321,214

(22) PCT Filed: May 12, 2010

(86) PCT No.: PCT/IB2010/052125
§ 371 (c)(1),
(2), (4) Date: Nov. 18, 2011

(87) PCT Pub. No.: WO2010/146483
PCT Pub. Date: Dec. 23, 2010

(65) Prior Publication Data
US 2012/0089377 A1    Apr. 12, 2012

Related U.S. Application Data

(60) Provisional application No. 61/218,088, filed on Jun. 18, 2009.

(51) Int. Cl.
G06F 17/50   (2006.01)
G06T 11/00   (2006.01)
A61B 6/03    (2006.01)
A61B 6/00    (2006.01)

(52) U.S. Cl.
CPC ............... *G06T 11/005* (2013.01); *A61B 6/032* (2013.01); *A61B 6/488* (2013.01)

(58) Field of Classification Search
None
See application file for complete search history.

(56) References Cited

U.S. PATENT DOCUMENTS

| 6,195,409 | B1 | 2/2001 | Chang et al. | |
| 7,443,393 | B2 * | 10/2008 | Shen et al. | 345/420 |
| 8,055,046 | B2 * | 11/2011 | Feilkas et al. | 382/131 |
| 8,086,027 | B2 * | 12/2011 | Kozakaya | 382/154 |
| 2005/0004446 | A1 | 1/2005 | Cowan et al. | |
| 2005/0171409 | A1 | 8/2005 | Arimura et al. | |
| 2006/0198499 | A1 * | 9/2006 | Spies et al. | 378/207 |

FOREIGN PATENT DOCUMENTS

| WO | 2004080309 A2 | 9/2004 |
| WO | 2007084789 A2 | 7/2007 |
| WO | 2008155738 A2 | 12/2008 |
| WO | 2009083864 A2 | 7/2009 |

OTHER PUBLICATIONS

Zheng et al., "Use of a dense surface point distribution model in a three-stage anatomical shape reconstruction from sparse information for computer-assisted orthopedic surgery: a preliminary study", ACCV 2006, Proceedings, Part II, 7th Asian Conference on Computer Vision, Jan. 2006, pp. 52-60.*
Krishnan et al., "A virtual study of shape-based optical reconstruction", in Biomedical Topical Meeting, OSA Technical Digest (Optical Society of America, 2004), paper WF45, Apr. 2004, 3 pages.*

* cited by examiner

*Primary Examiner* — Omar Fernandez Rivas
*Assistant Examiner* — Herng-Der Day

(57) ABSTRACT

A method includes generating with a processor (122) a three-dimensional subject specific model of structure of interest of a subject to be scanned based on a general three-dimensional model and pre-scan image data acquired by an imaging system (100) generating with the processor (122) an imaging plan for the subject based on the three-dimensional subject specific model.

18 Claims, 4 Drawing Sheets

IMAGING PROCEDURE PLANNING

CROSS REFERENCE TO RELATED APPLICATIONS

Figure 1:
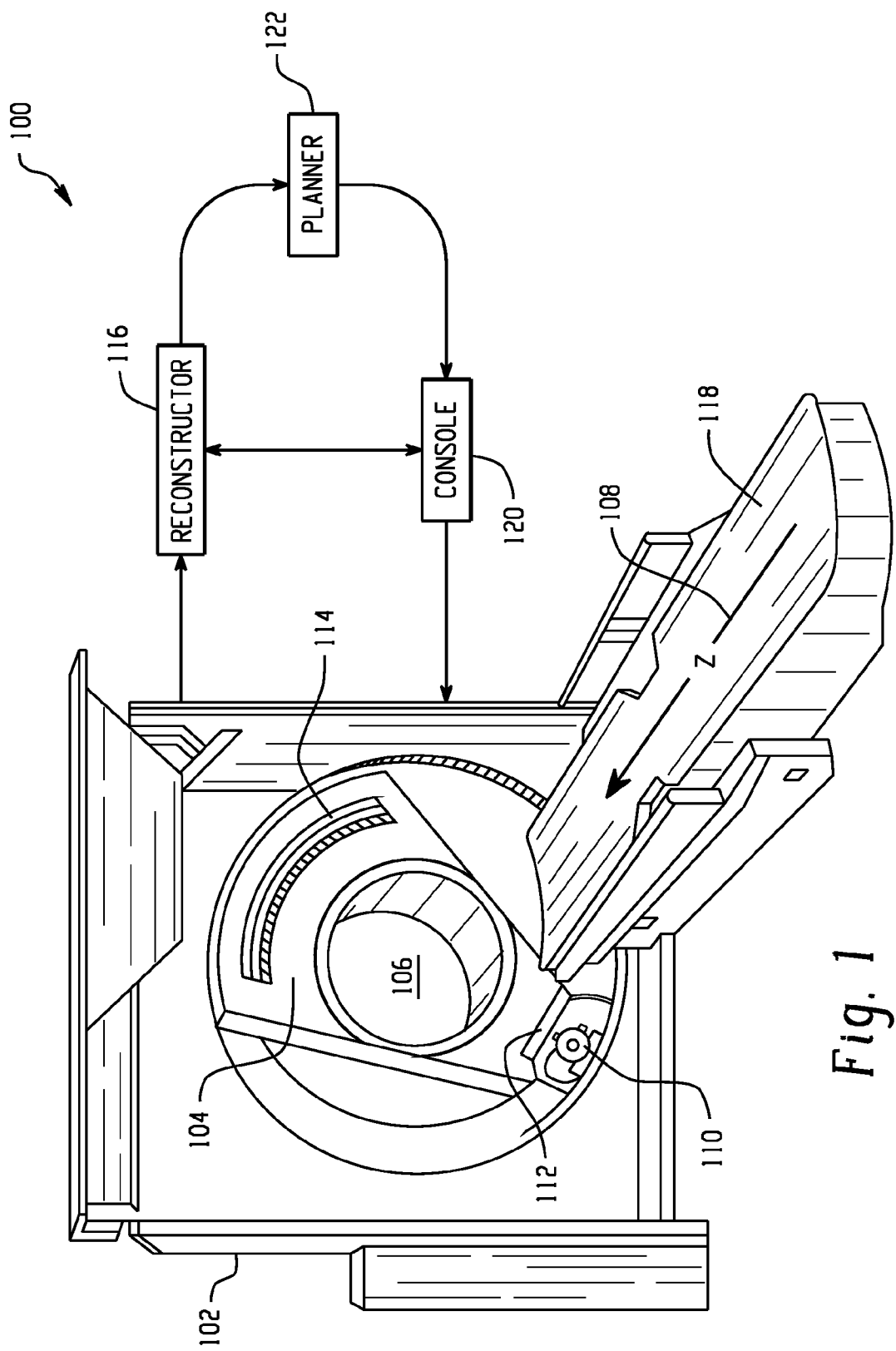

This application claims the benefit of U.S. provisional application Ser. No. 61/218,088 filed Jun. 18, 2009, which is incorporated herein by reference.

The following generally relates to imaging procedure planning and finds particular application to computed tomography (CT). However, it is also amenable to other medical imaging applications and to non-medical imaging applications.

A computed tomography (CT) scanner generally includes an x-ray tube that emits radiation that traverses an examination region and a patient supported therein via a patient support. A detector array detects radiation traversing the examination region and the patient. The detector array generates a signal indicative of the detected radiation. A reconstructor reconstructs the signal and generates volumetric image data indicative of the patient. The volumetric image data can be processed to generate one or more images of the patient. The one or more images can be displayed on a monitor and/or printed to film.

For planning an imaging procedure for the patient, a pre-scan covering a region of interest of the patient is first performed. The pre-scan typically involves scanning the patient with the x-ray tube fixed at angular position while advancing the patient through the examination region via the patient support. The pre-scan coverage generally is larger than the anticipated imaging procedure coverage and provides an image showing two-dimensional contours of the scanned anatomy. From the pre-scan, the operator can identify start and end scan locations along the z-axis for anatomy of interest. The image procedure is then performed based on a selected scan protocol and the start and end positions.

Unfortunately, the pre-scan image is a two-dimensional image, while the anatomy of the patient is three-dimensional. As such, the start and end scan positions for anatomy of interest may be difficult to identify from the pre-scan image. For example, a portion of the anatomy of interest may be behind other anatomy or otherwise obstructed such that the extent of the anatomy of interest is not clear. One solution is to add a margin to the plan or increase the z-axis coverage in order to ensure the anatomy of interest is scanned. However, this may lead to irradiating portions of the patient outside of the anatomy of interest and increasing patient dose.

Aspects of the present application address the above-referenced matters and others.

According to one aspect, a method includes generating with a processor a three-dimensional subject specific model of structure of interest of a subject to be scanned based on a general three-dimensional model and pre-scan image data acquired by an imaging system generating with the processor an imaging plan for the subject based on the three-dimensional subject specific model.

According to another aspect, a system includes a patient specific model generator that generates a patient specific three-dimensional anatomical model for a patient based on a general three-dimensional anatomical model and pre-scan image data and a planning component that generates an imaging plan for imaging the patient based on the patient specific three-dimensional anatomical model.

According to another aspect, a computer readable storage medium contains instructions which, when executed by a computer, cause the computer to perform the step of: planning a radiation therapy treatment based on an estimated applied dose determined from a patient specific three-dimensional anatomical model generated based on a general three-dimensional anatomical model and pre-scan image data.

According to another aspect, a computer readable storage medium contains instructions which, when executed by a computer, cause the computer to perform the step of: tracking a dose applied to an object or subject for a plurality of imaging procedures based on an estimated applied dose determined from a patient specific three-dimensional anatomical model that is generated based on a general three-dimensional anatomical model and pre-scan image data.

According to another aspect, a computer readable storage medium contains instructions which, when executed by a computer, cause the computer to perform the step of: planning an imaging plan based on a patient specific three-dimensional anatomical model generated based on a general three-dimensional anatomical model and pre-scan image data.

The invention may take form in various components and arrangements of components, and in various steps and arrangements of steps. The drawings are only for purposes of illustrating the preferred embodiments and are not to be construed as limiting the invention.

Figure 2:
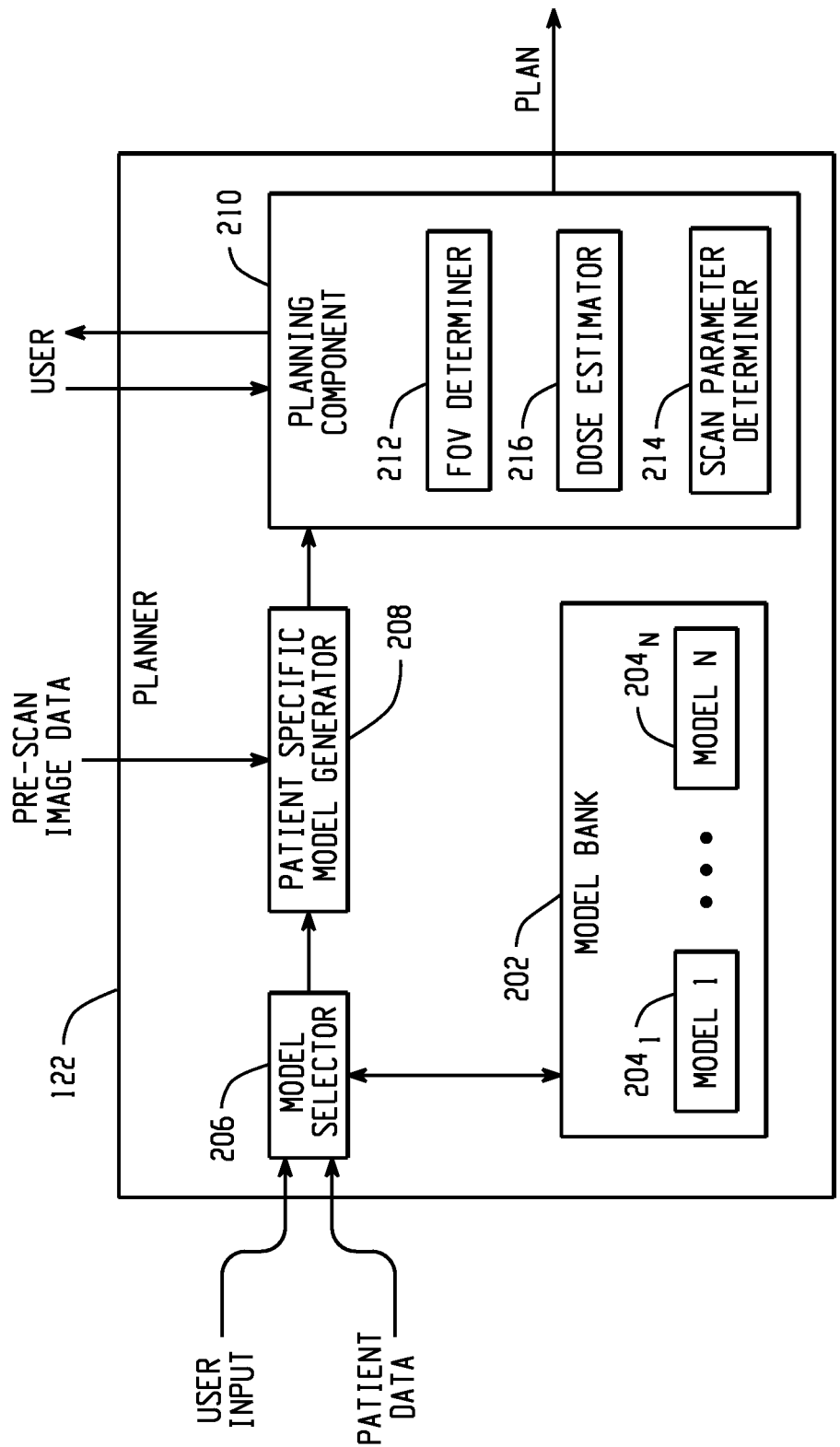
Figure 4:
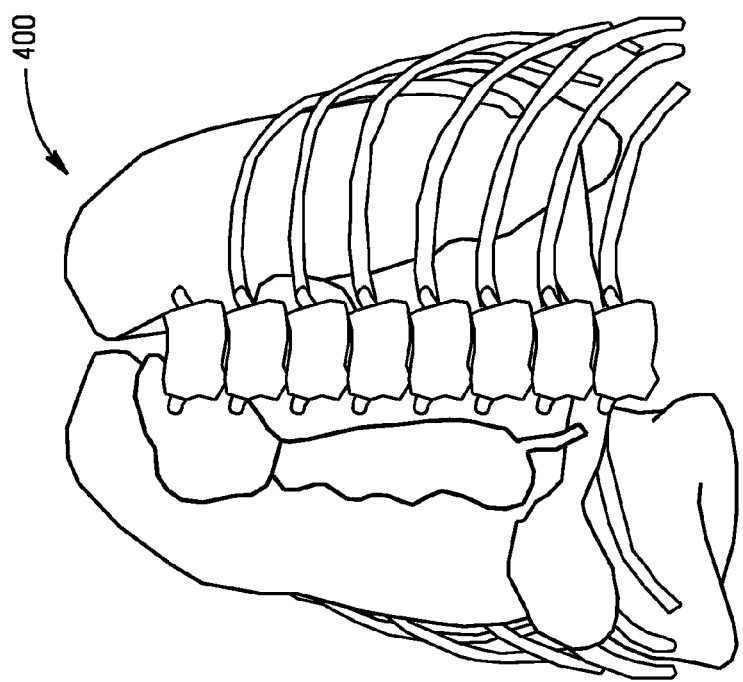
Figure 3:
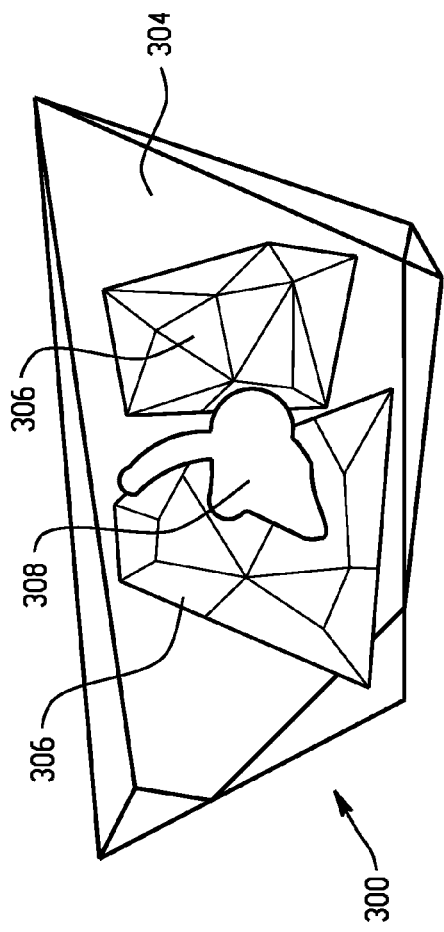
Figure 5:
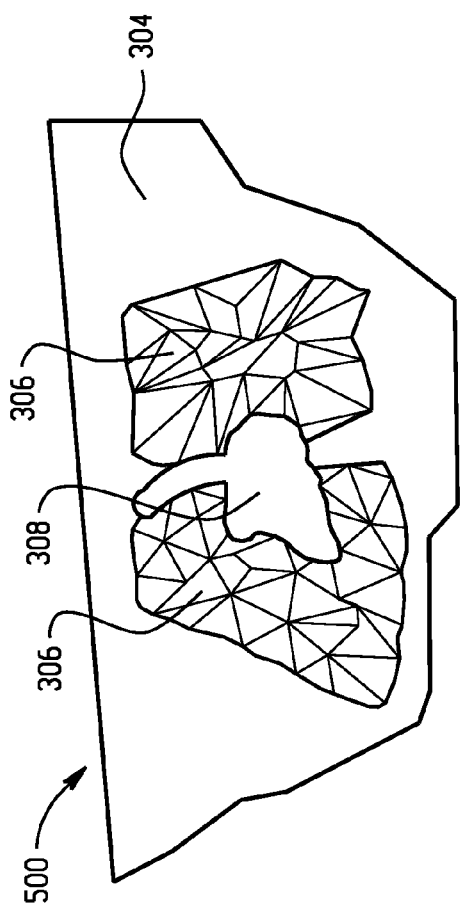
Figure 6:
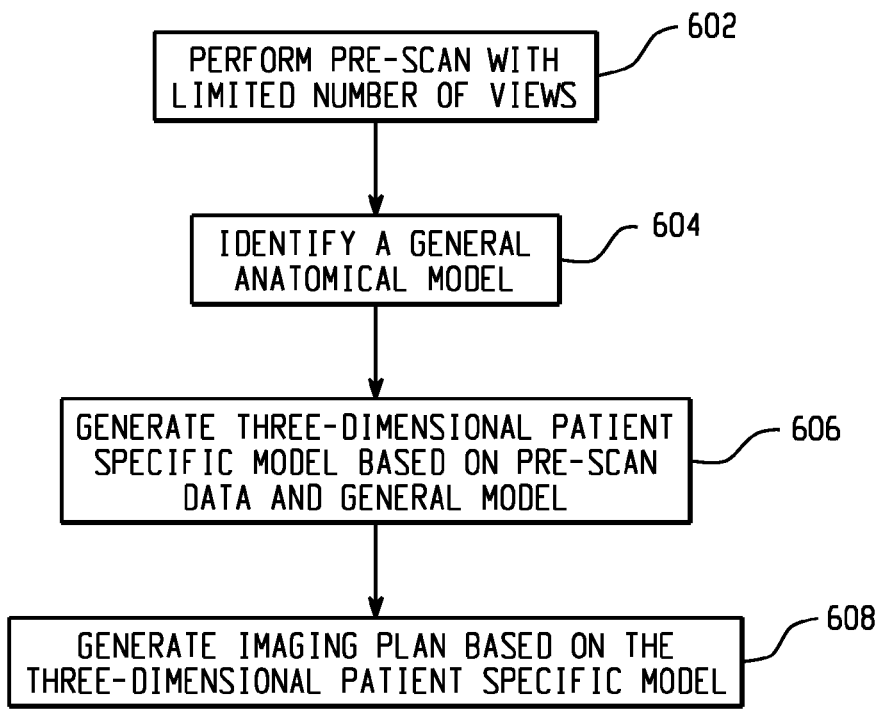
Figure 7:
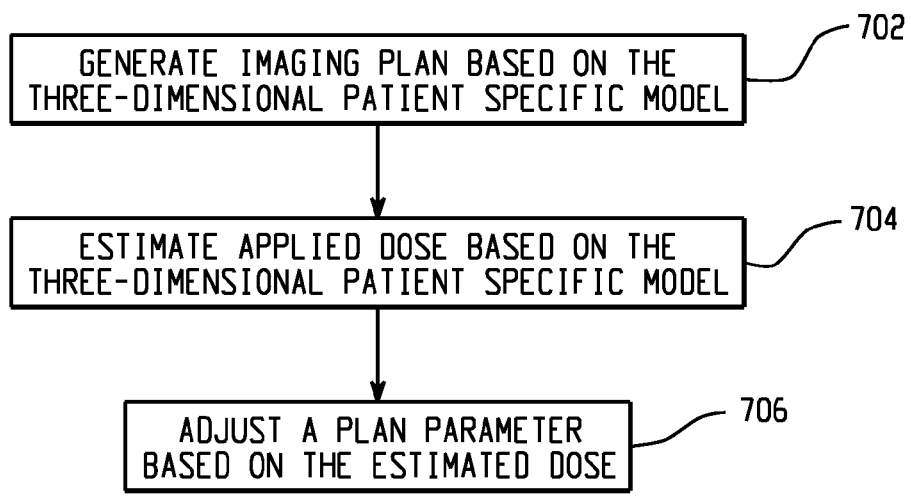

FIG. 1 illustrates an example imaging system.
FIG. 2 illustrates an example imaging procedure planner.
FIG. 3 illustrates an example of a simple three-dimensional anatomical model.
FIG. 4 illustrates an example of a three-dimensional patient specific anatomical model.
FIG. 5 illustrates an example of a complex three-dimensional anatomical model.
FIG. 6 illustrates an example method.
FIG. 7 illustrates an example method.

FIG. 1 illustrates an imaging system 100 such as a computed tomography scanner. The imaging system 100 includes a stationary gantry 102 and a rotating gantry 104, which is rotatably supported by the stationary gantry 102. The rotating gantry 104 is configured to alternatively rotate around an examination region 106 about a longitudinal or z-axis 108 or remain stationary with respect to the examination region 106 for scanning.

A radiation source 110 is supported by and rotates with the rotating gantry 104 around the examination region 106 about a z-axis 108. A collimator 112 collimates the emitted radiation to produce a generally conical, fan, wedge, or other shaped radiation beam. A radiation sensitive detector array 114 detects radiation that traverses the examination region 106 and generates a signal indicative thereof.

A reconstructor 116 reconstructs the projection data and generates volumetric image data indicative of the examination region 106. A patient support 118, such as a couch, supports the patient for the scan. A general purpose computing system 120 serves as an operator console. Software resident on the console 120 allows the operator to control the operation of the system 100.

The system 100 can be used to perform pre-scans and imaging procedures based thereon. Examples of pre-scans include scout scan in which the radiation source 110 remains stationary as the patient is advanced via the patient support 118, low-dose helical, axial (step and shoot) and/or other scan in which a relatively small number of views (e.g., 5 to 50) are acquired each rotation, and/or other pre-scans. Generally, a pre-scan can be used to facilitate planning or generating a plan for an imaging procedure of an object or subject.

A planner 122 allows a user such as a clinician or radiology technician to plan the imaging procedure for the object or subject. As described in greater detail below, in one instance the planner 122 generates a patient specific three-dimensional anatomical model based on a predetermined general three-dimensional anatomical model and three dimensional data from a pre-scan, such as a low dose spiral or helical scan. The generated three-dimensional model provides additional information for planning, relative to a configuration in which the system 100 does not employ the three-dimensional model.

In one instance, the additional information allows the operator to identify scan start and stop locations in three dimensions, which may lead to a more accurate z-axis coverage or field of view (FOV) for particular anatomy of interest. This, in turn, may reduce patient dose relative to a configuration in which the three dimensional model is not used to determine the start and stop locations. The generated three-dimensional model can also be used to estimate patient dose, adjust scan parameters such tube current and/or voltage modulation, facilitate planning a radiation therapy treatment, and/or to determine other information.

The illustrated planner 122 is shown separate from the system 100. In this instance, the planner 122 can be part of a dedicated workstation or general purpose computer in which a processor executes computer readable instructions stored on computer readable medium to generate the patient specific three-dimensional anatomical model and/or present a user interface through which a user can interact to set scan parameters, create the imaging procedure plan, etc. In another embodiment, the planner 122 can be part of the system 100, for example, an application executed by a processor of the console 120

FIG. 2 illustrates an example of the planner 122. The illustrated planner 122 includes a model bank 202 with N three-dimensional anatomical models 204$_1$ to 204$_N$, (collectively referred to herein as three-dimensional models 204), where N is an integer equal to or greater than one. One or more of the three-dimensional models 204 may be tailored towards patient age, gender, race, pathology, and/or other patient related information. The three-dimensional models 204 also may include a relatively simple three-dimensional model and/or a relatively complex three-dimensional model.

Briefly turning to FIG. 3, an example of a simple three-dimensional anatomical model 300 is illustrated. The three-dimensional model 300 includes a plurality of compartments representing various anatomical structures of interest. The illustrated three-dimensional model 300 includes compartments representing a body contour 304, lungs 306, and a heart 308. In other embodiment, the three-dimensional model 300 includes compartments representing more, less and/or one or more other anatomical structure.

In FIG. 3, a compartment is described via a number of parameters. For example, with one embodiment the parameters are described by three-dimensional coordinates of vertices, which constitute a triangular surface mesh of the compartment. In another embodiment, the parameters are described by geometric parameters controlling a shape of the compartment, such as radius, height, a length, a position, an orientation, etc. of a compartment. Other approaches are also contemplated herein.

Turning briefly next to FIG. 4, an example of a more complex three-dimensional anatomical model 400 is illustrated. This example includes several additional compartments representing different anatomical structures of interest such as lungs, liver, heart, rib cage, spine, diaphragm, thorax, etc.

Returning to FIG. 2, a model selector 206 selects a model 204 from the model bank 202 based on information such as patient data, user input, a predetermined default model, and/or other information.

A patient specific model generator 208 generates a three-dimensional patient specific anatomical model based on the selected model 204 and pre-scan image data such as image data from a low-dose scan with a limited number of views in each revolution, such as less than fifty (50) views.

In one instance, the patient specific model generator 208 employs an iterative algorithm, which fits the selected model 204 to the pre-scan image data to generate the patient specific model 204. A non-limiting example of a suitable algorithm is shown in EQUATION 1:

$$I = \sum_{j=1}^{N} \sum_{k=1}^{D} |p_{jk} - p_{jk}^{sim}(M)|^2, \qquad \text{EQUATION 1}$$

wherein I is an objective function, $p_{jk}^{sim}$ (M) represents a forward projection of model M onto the $k^{th}$ detector element, k=1, ..., D of projection view number j, and j=1, ..., N, and $p_{jk}$ represents a forward projection of pre-scan image data. EQUATION 1 is used to determine a difference between the selected model and the pre-scan image data and is iteratively used to determine the difference until a residual between the selected model and the pre-scan image data is minimized or a predetermined threshold is satisfied.

With EQUATION 1, model surfaces and constant mean absorption coefficients inside the model compartments are reconstructed. As such, a very low number of projections can be used for this algorithm In this example, the projections have an equal angular distribution and a full coverage of the object of interest along the rotation axis. In another embodiment, projections do not have equal angular distribution and/or full coverage of the object of interest along the rotation axis.

In another embodiment, the objective function is minimized with a gradient descent algorithm with respect to the vertex-coordinates of a surface mesh model. In yet another embodiment, the parameters to be optimized are given as shape parameters like radius, length, position, orientation of geometric bodies (sphere, cylinder, ellipsoid). In still other embodiments, other approaches are employed.

Another suitable technique for generating the three-dimensional patient specific anatomical model is described in international patent application serial number PCT/IB2008/0955348, filed Dec. 16, 2008, and entitled "ITERATIVE RECONSTRUCTION OF POLYHEDRAL OBJECTS FROM FEW PROJECTIONS," the entirety of which is incorporated herein by reference.

Briefly turning to FIG. 5, an example three-dimensional patient specific anatomical model 500 is illustrated. The illustrated patient specific anatomical model 500 is generated based on the three-dimensional anatomical model 300 (FIG. 3) and the pre-scan image data. Note that the compartment shapes in the patient specific anatomical model 500 are not the same as the compartment shapes in the three-dimensional anatomical model 300.

The patient specific anatomical model 500 can be stored in local memory and/or remote memory such as in a remote database or archival system like a Picture Archiving and Communication System (PACS), a Radiology Information System (RIS), a Hospital Information System (HIS), and/or data repository. The stored information can be used for follow up studies, examinations with different modalities, further processing, and/or otherwise. For example, the patient specific anatomical model 500 can be used for image registration between different imaging modalities.

With reference to FIGS. 2 and 5, a planning component 210 facilitates planning the imaging procedure. In the illustrated embodiment, this includes utilizing the three-dimensional patient specific anatomical model 500 to determine a suitable scan coverage or a field of view (FOV) for scanning the anatomical tissue of interest. In one instance, the FOV is identified by presenting the three-dimensional patient specific anatomical model 500 via a display, monitor or the like and receiving input indicative of the desired FOV.

By way of example, in one non-limiting instance the three-dimensional patient specific anatomical model 500 is displayed on a display and a user identifies through a mouse, a keypad, and/or other input device a scan start location and a scan end location (FOV) based on the three-dimensional patient specific anatomical model 500. In this instance, the user can translate and/or rotate the three-dimensional patient specific anatomical model 500 to identify the start and stop locations. Similar to the three-dimensional patient specific anatomical model 500, the FOV can be stored in local and/or remote memory.

In another instance, the FOV is identified by a FOV determiner 212. In the illustrated embodiment, the FOV determiner 212 determines a center of mass of a user or otherwise identified compartment corresponding to an anatomical region of interest in the patient specific anatomical model 500 and defines the FOV about the center of mass. For a surface mesh based model, this can be achieved by computing the center of mass of the vertices belonging to the compartment of interest. For a geometric based model, various compartments of interests can be extracted from model parameters such as position, orientation, length, radius, etc.

A dose estimator 216 estimates an applied dose of the individual compartments of the model and/or an aggregate dose of the compartments based on the FOV, the three-dimensional patient specific anatomical model 500, and/or a simulation based on the model 500. Similar to the patient specific anatomical model 500 and the FOV, the estimated dose can be stored in local and/or remote memory. The stored dose information can be used to track overall total patient dose, with follow-up exams, in connection with radiation therapy planning, etc. For example, a radiation therapy treatment plan can be generated based on the estimated applied dose.

A scan parameter determiner 214 determines various scan parameters based on the FOV, the estimated dose and/or the three-dimensional patient specific anatomical model 500. Examples of such parameters include, but are not limited to, a tube current modulation, a tube voltage modulation, scanning pitch, and/or one or more other scan parameters. The scan parameter determiner 214 can determine one or more of the scan parameters automatically or based on user input and/or interaction.

In one instance, a view-dependent dose modulation can be derived from the three-dimensional patient specific anatomical model 500 by optimizing the tube's voltage and current. For example, projection directions with large and small attenuation can be identified from the model 500 and the appropriate tube settings can be view and patient specific. As such, both under and overflow of the detector signal can be avoided and the dose per view can be adjusted to yield a maximum image quality at minimum applied overall dose.

FIG. 6 illustrates an example method.

At 602, a pre-scan of a region of interest of an object or subject is performed. As described herein, the pre-scan can be a helical, an axial, etc. scan with relatively low dose and a small number of views for each rotation.

At 604, a general three-dimensional model is identified for the patient. As described herein, the selected model may be tailored towards the age, gender, race, and/or other characteristic of the patient.

At 606, a patient specific three-dimensional model is generated based on the selected general three-dimensional model and the data from the pre-scan. As described herein, this may include fitting the general three-dimensional patient model to the patient anatomy of the pre-scan using an adaptive algorithm that adapts the general three-dimensional model to the patient anatomy.

At 608, an imaging plan is generated based on the three-dimensional patient specific model. This includes determining a scan field of view (FOV) based on the three-dimensional patient specific model.

In another embodiment, act 602 is omitted, and the pre-scan data is obtained from another system, a data repository, etc.

FIG. 7 illustrates another example method.

At 702, an imaging plan is generated based on the three-dimensional patient specific model, which is generated based on a general three-dimensional anatomical model and pre-scan image data, as described in connection with FIG. 6.

At 704, an applied dose to the structure of the object or subject is estimated based the three-dimensional patient specific anatomical model 500 and/or a simulation based thereon.

At 706, the estimated applied dose is used to adjust one or more parameters of the imaging plan. As described herein, suitable parameters include, but are not limited to, a tube current modulation, a tube voltage modulation, a scanning pitch, etc.

The above may be implemented by way of computer readable instructions, which, when executed by a computer processor(s), causes the processor(s) to carry out the acts described herein. In such a case, the instructions are stored in a computer readable storage medium such as memory associated with and/or otherwise accessible to the relevant computer.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

What is claimed is:

1. A method, comprising:
generating with a processor a three-dimensional subject specific model of a structure of interest of a subject to be scanned by fitting a forward projection of an anatomical three-dimensional model to a forward projection of pre-scan image data from a low-dose helical three-dimensional scan acquired by an imaging system based on:

$$I = \sum_{j=1}^{N} \sum_{k=1}^{D} |p_{jk} - p_{jk}^{sim}(M)|^2,$$

wherein I is an objective function, $p_{jk}^{sim}(M)$ represents the forward projection of the anatomical three-dimensional model M onto a $k^{th}$ detector element, $k = 1, \ldots, D$ of projection view number $j$, $j=1, \ldots, N$, and $p_{jk}$ represents the forward projection of the low-dose helical three-dimensional pre-scan image data, which iteratively minimizes differences between the forward projection of the low-dose helical three-dimensional pre-scan image data and the forward projection of the anatomical three-dimensional model onto detector elements of projection views; and generating with the processor an imaging plan for the subject based on the three-dimensional subject specific model.

2. The method of claim 1, wherein the low-dose helical three-dimensional pre-scan image data includes less than fifty views of the structure of interest in each rotation of a detector array.

3. The method of claim 1, further comprising: stopping the iteratively fitting in response to the difference satisfying a predetermined threshold and outputting the generated three-dimensional subject specific model.

4. The method of claim 1, further comprising:
displaying the three-dimensional subject specific model;
accepting a user input indicative of a change to the plan, wherein the change is based on the three-dimensional subject specific model; and
updating the plan based on the user input.

5. The method of claim 1, further comprising: determining a scan field of view for the imaging plan based on the three-dimensional subject specific model.

6. The method of claim 1, further comprising: estimating an applied dose for the subject to be scanned using the imaging plan based on the three-dimensional subject specific model.

7. The method of claim 1, wherein the anatomical three-dimensional model is defined by a plurality of compartment described by three-dimensional coordinates of vertices that constitute a triangular surface mesh of the compartments.

8. The method of claim 1, wherein the anatomical three-dimensional model is defined by a plurality of compartments described by geometric parameters controlling a shape of the compartments.

9. A system, comprising:
a patient specific model generator, implemented through a hardware processor, that generates a patient specific three-dimensional anatomical model for a patient by fitting a forward projection of an anatomical three-dimensional model to a forward projection of pre-scan image data from a low-dose helical three-dimensional scan based on:

$$I = \sum_{j=1}^{N} \sum_{k=1}^{D} |p_{jk} - p_{jk}^{sim}(M)|^2,$$

wherein I is an objective function, $p_{jk}^{sim}(M)$ represents the forward projection of the anatomical three-dimensional model M onto a $k^{th}$ detector element, $k=1, \ldots, D$ of projection view number j, $j=1, \ldots, N$, and $p_{jk}$ represents the forward projection of the pre-scan image data, which iteratively minimizes differences between the forward projection of the pre-scan image data and the forward projection of the anatomical three-dimensional model onto detector elements of projection views; and
a planning component, implemented through the hardware processor, that generates an imaging plan for imaging the patient based on the patient specific three-dimensional anatomical model.

10. The system of claim 9, wherein the patient specific model generator generates the patient specific three-dimensional anatomical model by changing the anatomical three-dimensional model to fit the pre-scan image data.

11. The system of claim 9, further comprising a field of view determiner that determines a scan field of view for the imaging plan based on the patient specific three-dimensional anatomical model.

12. The system of claim 9, further comprising a dose estimator that estimates an applied dose for the imaging plan based on the patient specific three-dimensional anatomical model.

13. The system of claim 12, further comprising a scan parameter determiner that determines at least one of a tube current or voltage modulation based on the patient specific three-dimensional anatomical model and the estimated applied dose.

14. The system of claim 9, wherein the patient specific three-dimensional anatomical model and the anatomical three-dimensional model are defined by mesh or geometric parameters.

15. A non-transitory computer readable storage medium containing instructions which, when executed by a computer, cause the computer to perform the step of:
planning a radiation therapy treatment based on an estimated applied dose determined from a patient specific three-dimensional anatomical model which is generated by fitting a forward projection of a three-dimensional anatomical model to a forward projection of pre-scan image data from a low-dose helical three-dimensional scan based on:

$$I = \sum_{j=1}^{N} \sum_{k=1}^{D} |p_{jk} - p_{jk}^{sim}(M)|^2,$$

wherein I is an objective function, $p_{jk}^{sim}(M)$ represents the forward projection of the three-dimensional anatomical model M onto a $k^{th}$ detector element, $k=1, \ldots, D$ of projection view number j, $j=1, \ldots, N$, and p represents the forward projection of the low-dose helical three-dimensional pre-scan image data, which iteratively minimizes differences between the forward projection of the low-dose helical three-dimensional pre-scan image data and the forward projection of the three-dimensional anatomical model onto detector elements of projection views.

16. The computer readable storage medium of claim 15, wherein the patient specific three-dimensional anatomical model includes a plurality of compartments, each compartment representing an anatomical structure of interest, and the estimated applied dose is estimated for each compartment.

17. A non-transitory computer readable storage medium containing instructions which, when executed by a computer, cause the computer to perform the step of:
generating an imaging plan based on a patient specific three-dimensional anatomical model generated by fitting a forward projection of an anatomical three-dimensional model and a forward projection of pre-scan image data from a low-dose helical three-dimensional scan based on:

$$I = \sum_{j=1}^{N} \sum_{k=1}^{D} |p_{jk} - p_{jk}^{sim}(M)|^2,$$

wherein I is an objective function, $p_{jk}^{sim}(M)$ represents the forward projection of the anatomical three-dimensional model M onto a $k^{th}$ detector element, k=1, ..., D of projection view number j, j=1, ..., N, and $p_{jk}$ represents the forward projection of the low-dose helical three-dimensional pre-scan image data, which iteratively minimizes differences between the forward projection of the low-dose helical three-dimensional pre-scan image data and the forward projection of the anatomical three-dimensional model onto detector elements of projection views.

18. The computer readable storage medium of claim 17, further containing instructions which, when executed by the computer, cause the computer to perform the steps of:

accepting an input indicative of a change to the imaging plan; and updating the plan to reflect the change.

* * * * *